United States Patent [19]
Field

[11] Patent Number: 5,919,183
[45] Date of Patent: Jul. 6, 1999

[54] INTRODUCERS AND ASSEMBLIES

[75] Inventor: Stephen James Field, Bridge, United Kingdom

[73] Assignee: Smiths Industries Public Limited Company, London, United Kingdom

[21] Appl. No.: 08/842,055

[22] Filed: Apr. 23, 1997

[30] Foreign Application Priority Data

Apr. 25, 1996 [GB] United Kingdom .................... 9608483

[51] Int. Cl.$^6$ .................................................. A61M 25/00
[52] U.S. Cl. ........................................... 604/530; 604/536
[58] Field of Search ................................... 600/581, 585, 600/120, 170, 194; 604/167, 170, 282, 164

[56] References Cited

U.S. PATENT DOCUMENTS

| | | | |
|---|---|---|---|
| 3,957,055 | 5/1976 | Linder et al. ............................ | 128/351 |
| 4,634,432 | 1/1987 | Kocak ...................................... | 604/167 |
| 4,817,613 | 4/1989 | Jaraczewski et al. ................... | 604/282 |
| 4,897,079 | 1/1990 | Zaleski et al. ............................ | 604/43 |
| 4,911,691 | 3/1990 | Aniuk et al. ............................. | 604/164 |
| 4,983,170 | 1/1991 | Etheredge, III et al. ................ | 604/270 |
| 5,015,238 | 5/1991 | Solomon et al. ......................... | 604/164 |
| 5,085,649 | 2/1992 | Flynn ....................................... | 604/264 |
| 5,266,669 | 11/1993 | Onwunaka et al. ...................... | 528/28 |
| 5,342,383 | 8/1994 | Thomas .................................... | 606/190 |
| 5,395,332 | 3/1995 | Ressemann et al. ..................... | 604/96 |
| 5,397,302 | 3/1995 | Weaver et al. ............................ | 604/54 |
| 5,443,907 | 8/1995 | Slaikeu et al. ........................... | 428/375 |
| 5,489,269 | 2/1996 | Aldrich et al. ............................ | 604/95 |
| 5,599,305 | 2/1997 | Hermann et al. ......................... | 604/53 |
| 5,643,174 | 7/1997 | Yamamoto et al. ...................... | 600/114 |
| 5,704,926 | 1/1998 | Sutton ...................................... | 604/282 |
| 5,752,937 | 5/1998 | Otten et al. .............................. | 604/161 |
| 5,762,630 | 6/1998 | Bley et al. ................................ | 604/264 |

FOREIGN PATENT DOCUMENTS

| | | |
|---|---|---|
| 0 606 832 A2 | 7/1994 | European Pat. Off. . |
| WO 84/04664 | 12/1984 | WIPO . |
| WO 93/19807 | 10/1993 | WIPO . |

*Primary Examiner*—Wynn Wood Coggins
*Assistant Examiner*—Sharon Finkel
*Attorney, Agent, or Firm*—Pollock, Vande Sande & Amernick

[57] ABSTRACT

An introducer, such as for an endotracheal tube, comprises a solid rod made of an aliphatic polyurethane containing about 20% barium sulphate. The hardness of the material is about 60 Shore D so that the introducer is resilient within a range of deformation and beyond this range it is bendable into a set shape that only resumes its original shape at a slower rate.

6 Claims, 2 Drawing Sheets

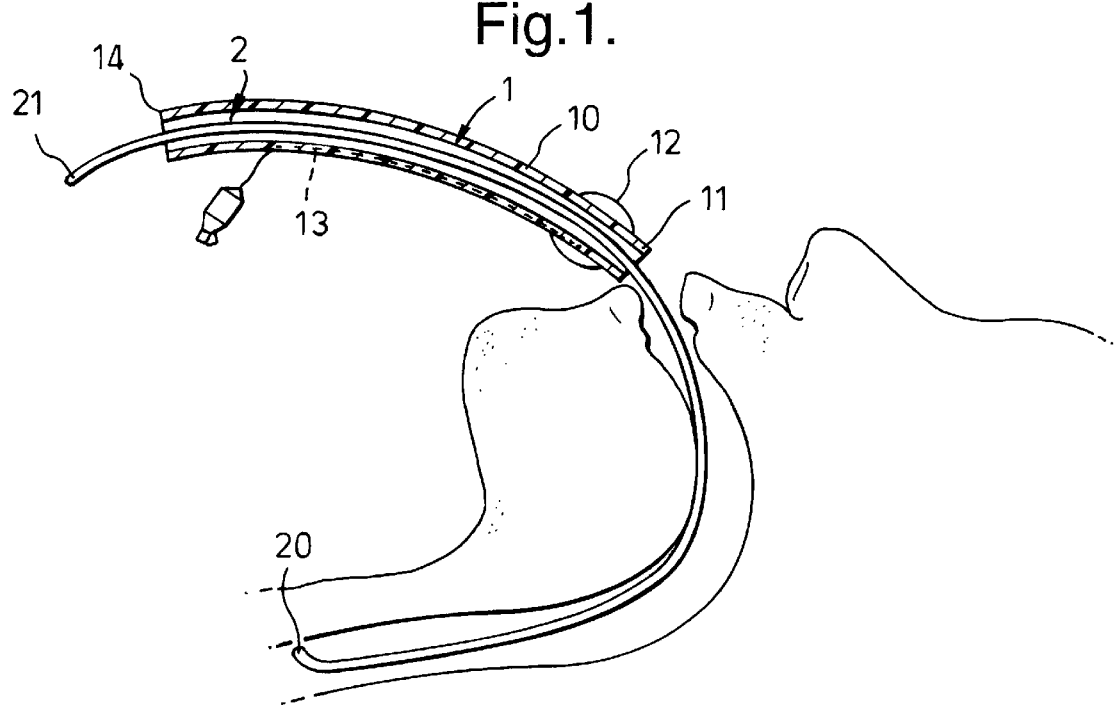
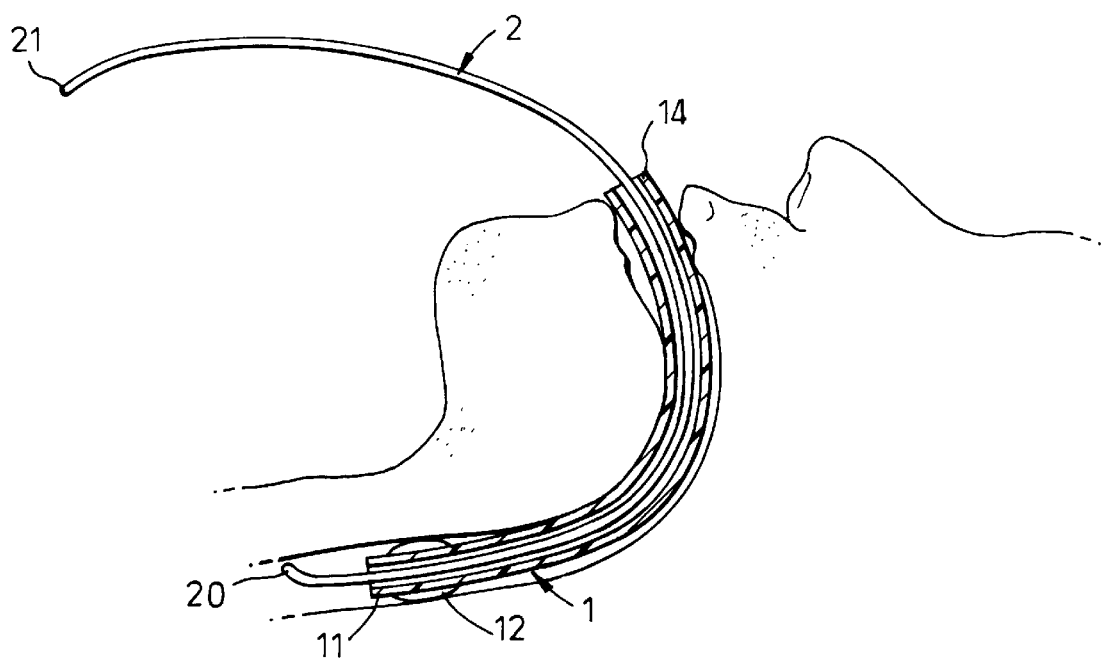

INTRODUCERS AND ASSEMBLIES

BACKGROUND OF THE INVENTION

This invention relates to introducers and assemblies including introducers.

The invention is more particularly concerned with introducers of the kind used to assist intubation of medical tubes, such as endotracheal tubes.

Where the insertion route for a tracheal tube cannot be clearly seen, it is often necessary to use an introducer to help ensure correct intubation. The introducer takes the form of a rod that can be bent to a desired shape. The introducer can be inserted more easily than the tube because it can be bent to a desired shape and it has a smaller diameter. The smaller diameter of the introducer also enables a better view of the trachea. Once correctly inserted, a tube can be slid along the introducer into the correct location. A similar device can also be used as a stylet to assist introduction, by inserting it in the tube before the tube is inserted in the patient. The tube and introducer are bent to a shape that facilitates insertion, and the tube and introducer are then inserted together. Preferably, the introducer only takes the desired shape temporarily and returns close to its original shape after insertion, so that the introducer can be removed easily from the tube without disturbing it. Also, the introducer is softened by the heat of body, thereby making removal easier.

Introducers are also used as guides when a tube needs to be changed, if the original intubation was difficult. An introducer with a plain end is inserted into the tube before removal and the tube is then slid out along the introducer, while this remains in place. A new tube is then slid in along the introducer.

One example of a conventional tracheal tube introducer is sold by Eschmann Healthcare of Hythe, Kent, England under catalogue number 14-504-17. This introducer is made by braiding a sleeve from polyester filament on a mandrel, which is then repeatedly coated with a resin and dried in an oven. The mandrel is removed after a f ew coats and the coating and drying stage is repeated over twenty times to give the introducer the desired handling properties. This is a labour-intensive and expensive process.

BRIEF SUMMARY OF THE INVENTION

It is an object of the present invention to provide an introducer that can be made more easily.

According to one aspect of the present invention there is provided a medical tube introducer comprising an elongate member substantially of an aliphatic polyurethane material, the material being selected such that the introducer is resilient within a range of deformation and beyond this range it is bendable into a set shape that only resumes its original shape at a slower rate.

The introducer is preferably a solid rod, and the material may have a hardness between about 50 Shore A to 80 Shore D, preferably about 60 Shore D. The material may contain barium sulphate, such as at about 20%. The introducer may have a braided outer sleeve covered by a coating. The introducer may have a bend at its patient end.

Alternatively, the introducer may be a hollow rod.

According to another aspect of the present invention there is provided an assembly of a medical tube and an introducer according to the above one aspect of the invention. The tube may be an endotracheal tube.

An introducer and an assembly including an introducer, according to the present invention, will now be described, by way of example, with reference to the accompanying drawings.

BRIEF DESCRIPTION OF THE DRAWINGS

FIG. 1 is a cross sectional side elevation view of the introducer and an endotracheal tube, with the introducer inserted in the patient and the tube not yet inserted;

FIG. 2 is a cross sectional side elevation view of the introducer and tube, with the tube also inserted.

DETAILED DESCRIPTION OF THE PREFERRED EMBODIMENTS

Figure 3:
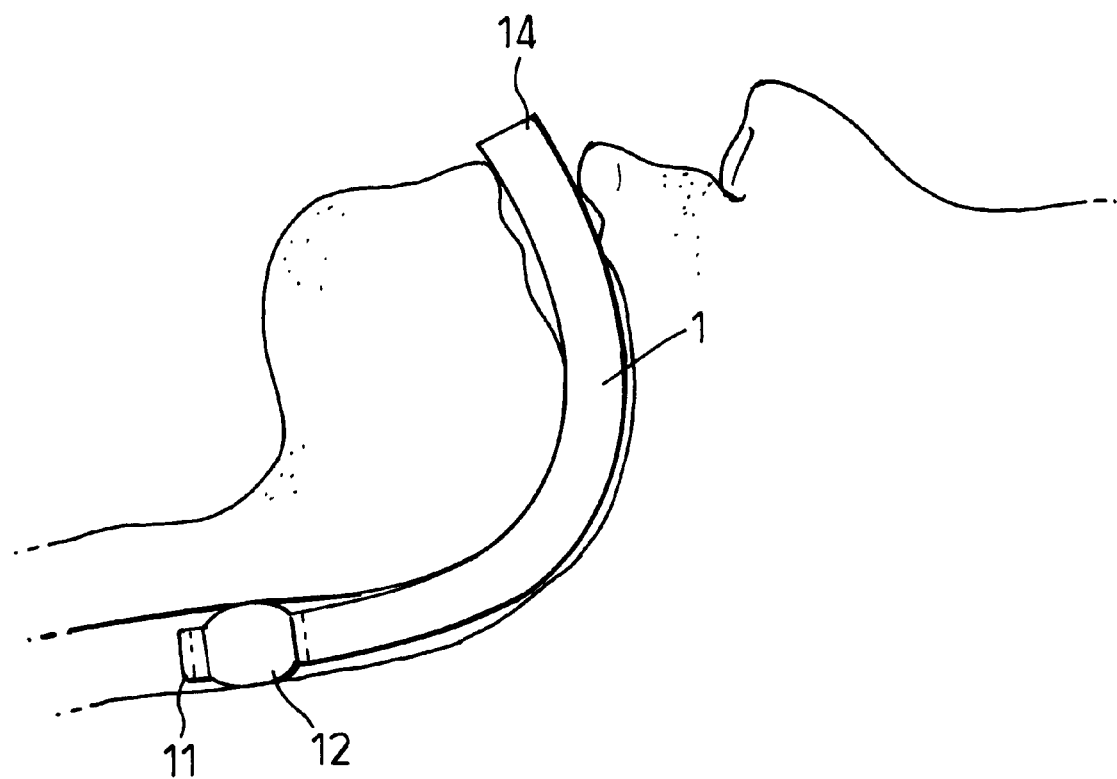
FIG. 3 is a partly sectional side elevation showing the tube after removal of the introducer.

With reference to FIG. 1, there is shown an endotracheal tube 1 and an introducer 2, with one end 20 of the introducer inserted in the patient and with the tube threaded on the other end of the introducer, externally of the patient.

The endotracheal tube 1 is of conventional form, having an extruded, tubular shaft 10 of a plastics material, such as PVC, and curved along its length to a circular arc. An inflatable cuff 12 embraces the shaft 10 close to the patient end and can be inflated by means of air supplied via an inflation lumen 13 extruded within the wall of the shaft. The tube 1 is bendable but, in its natural state, takes up a curved form that follows approximately the shape of the patient's anatomy. The material of the shaft 10 softens slightly at body temperature to enable the tube to bend more readily when in location. In use, the patient end 11 of the tube 1 is inserted through the patient's mouth so that it extends through the vocal folds and is located in the trachea, with the machine end 14 of the tube projecting from the patient's mouth.

The introducer 2 is a rod of circular section about 720 mm long and about 5 mm in diameter, although other sizes could be used. The ends 20 and 21 of the introducer 2 are smoothly rounded to make them atraumatic. In its natural state, the introducer is straight and the patient end 20 may be preformed, as shown, during manufacture with an optional Coude tip, that is, a short length bent at an angle of about 40°. The introducer is made of an aliphatic polyurethane loaded with 20% by weight barium sulphate and has a hardness of 60 Shore D. This material is available from Thermedics Inc of Woburn, Mass., USA under the trade mark TECOFLEX, code number EG60D B20. The introducer 2 is made by extruding and then heat forming the tips 20 and 21, although it could be made by other techniques, such as injection moulding.

The introducer 2 has a relatively hard feel and is resiliently flexible when bent to a certain extent, resuming its initial shape rapidly when released, behaving like a conventional resilient element. If, however, the introducer is bent beyond this resilient limit, such as, to a radius of less than about 10 cm, it behaves differently. When first released, the introducer behaves resiliently, moving rapidly to a certain extent, and then it returns considerably more slowly, having, in effect taken a set or memory of the shape to which it was deformed. The mechanical performance of the introducer could be equated to a series connection of two springs, one of which is heavily damped.

The introducer 2 is used mainly in cases of difficult intubation, where the route for the tracheal tube 1 cannot be easily seen. The patient end 20 of the introducer 2 is first bent to the desired shape, which will usually be a shape having a smaller radius of curvature, as shown in FIG. 1, so that the patient end of the introducer enters the trachea instead of the oesophagus during insertion. The user bends the introducer 2 to shape immediately before introducing it into the trachea and bends it initially beyond the desired shape, because of the initial resilient return when first released. The relatively small diameter of the introducer 2 enables it to be inserted correctly more easily than the larger diameter tube 1. Insertion is also aided by the bend in the introducer 2 and by its smaller diameter, which makes it easier to see the patient end of the introducer during insertion. After the initial resilient return, the introducer 2 tends to return to its original shape but this is prevented, in part, by the constraint of the anatomy. The tracheal tube 1 is then slid along the introducer 2 until its patient end 11 is correctly located in the trachea, leaving the machine end 14 protruding a short distance from the patient's mouth, as shown in FIG. 2. The tube 1 is more bendable than the introducer 2 so that it conforms to the shape of the introducer. The introducer 2 is then pulled out, whilst holding the tube 1, to leave the tube in position, as shown in FIG. 3. This technique of introduction is the same as with conventional introducers.

The introducer may be made from an aliphatic polyurethane with a different hardness although generally the range 50 Shore A to 80 Shore D will be the most satisfactory. The introducer need not be a solid rod but could be a tube, so that the bore of the tube could be used, for example, for oxygen insufflation or to monitor carbon dioxide levels to detect for correct positioning of the tube. When the introducer is a tube, it will generally need to be made from a harder material because of its thinner wall, up to about 90 Shore D. The introducer need not be entirely of an aliphatic polyurethane. It could, for example, have a tip of a softer material or a coating of a different material. A braided outer sleeve could be placed on the body of the introducer and the introducer then dip coated in a varnish, such as an aqueous polyurethane or an alkyd resin varnish. The use of the braid would improve the torsional rigidity of the introducer compared with a plain aliphatic polyurethane rod. Fewer coatings would be needed than with conventional introducers made entirely from a resincoated braided sleeve.

A similar device could be used to assist introduction of a tracheal tube by acting as a stylet, that is, by being inserted into the tube and bending the assembly of the tube and stylet to the desired shape. The assembly of the introducer and the tube are then inserted together into the trachea. The introducer device/stylet is removed after correct location, leaving the tube in position. With such an arrangement, the purpose of the introducer device is to enable the tube to be bent to a shape that facilitates insertion. The hardness of such a device is preferably about 72 Shore D with the addition of about 20% barium sulphate to increase the stiffness and make it more opaque to X-rays.

The invention is not limited to introducers for tracheal tubes but could be used for introducers for introducing other tubes.

The present invention enables an introducer to be made with a considerable saving in manufacturing time and cost compared with conventional braided introducers, even when a braided outer sleeve is used.

What I claim is:

1. An assembly comprising: a medical tube, said medical tube is an endotracheal tube adapted and sized for insertion into the trachea and having a bore extending along its length; and an introducer, said introducer extending along the bore of said tube, wherein said introducer is a solid rod, said rod being of an aliphatic polyurethane material, and wherein said material is selected such that said assembly is resilient within a range of deformation and beyond this range it is bendable into a set shape that resumes its original shape at a slower rate.

2. An assembly according to claim 1, wherein said material has a hardness between about 50 Shore A and 80 Shore D.

3. An assembly according to claim 2, wherein said material has a hardness of about 60 Shore D.

4. An assembly according to claim 1, wherein said material contains barium sulphate.

5. An assembly according to claim 4, wherein said material contains about 20% barium sulphate.

6. An assembly according to claim 1, wherein said assembly has a bend at its patient end.

* * * * *